United States Patent
Vasandani et al.

(10) Patent No.: US 12,171,533 B2
(45) Date of Patent: Dec. 24, 2024

(54) AUTOMATIC CUFF IDENTIFICATION SYSTEM AND METHOD

(71) Applicant: Zimmer, Inc., Warsaw, IN (US)

(72) Inventors: Paresh M. Vasandani, Warsaw, IN (US); Douglas C Barker, Canton, OH (US)

(73) Assignee: Zimmer, Inc., Warsaw, IN (US)

( * ) Notice: Subject to any disclaimer, the term of this patent is extended or adjusted under 35 U.S.C. 154(b) by 496 days.

(21) Appl. No.: 17/176,932

(22) Filed: Feb. 16, 2021

(65) Prior Publication Data
US 2021/0251500 A1    Aug. 19, 2021

Related U.S. Application Data

(60) Provisional application No. 62/977,576, filed on Feb. 17, 2020.

(51) Int. Cl.
*A61B 5/0235* (2006.01)
*A61B 17/00* (2006.01)
(Continued)

(52) U.S. Cl.
CPC ........ *A61B 5/0235* (2013.01); *A61B 17/1325* (2013.01); *A61B 5/02* (2013.01);
(Continued)

(58) Field of Classification Search
CPC . A61B 5/0235; A61B 17/1325; A61B 5/7257; A61B 2017/00544;
(Continued)

(56) References Cited

U.S. PATENT DOCUMENTS

| 6,171,254 B1 | 1/2001 | Skelton |
|---|---|---|
| 2003/0167070 A1 | 9/2003 | Mcewen et al. |

(Continued)

FOREIGN PATENT DOCUMENTS

| EP | 2420186 A1 | 2/2012 |
|---|---|---|
| WO | WO-2007057639 A1 | 5/2007 |

(Continued)

OTHER PUBLICATIONS

Xiamen Better Silicone Rubber Co., Ltd, "Cross Slit Valve", published on Aug. 3, 2019, published at https://www.silicongasket.com/Cross-Slit-Valve-pd45606066.html (Year: 2019).*

(Continued)

*Primary Examiner* — Matthew Kremer
*Assistant Examiner* — Jonathan Drew Moroneso
(74) *Attorney, Agent, or Firm* — SCHWEGMAN LUNDBERG & WOESSNER, P.A.

(57) ABSTRACT

A system and method for automatic determination of type of pneumatic cuff is disclosed. A system can include a pneumatic cuff with an integrated valve, and a console connectable to the pneumatic cuff. The console can be a pneumatic control system that can include a processor and memory including instructions, which when executed by the processor causes the processor to: inflate the pneumatic cuff through the integrated valve past a threshold pressure such that the integrated valve opens, receive sensor data indicative of a pressure curve during inflation of the pneumatic cuff, compare the pressure curve to stored pressure curves, determine a recommendation, based on the comparison, including information verifying the type of pneumatic cuff attached, and output the recommendation to a user.

15 Claims, 13 Drawing Sheets

(51) Int. Cl.
*A61B 17/12* (2006.01)
*A61B 17/132* (2006.01)
*A61B 17/135* (2006.01)
*A61B 5/00* (2006.01)
*A61B 5/02* (2006.01)
*A61B 5/021* (2006.01)
*A61B 5/022* (2006.01)
*A61H 9/00* (2006.01)

(52) U.S. Cl.
CPC ............... *A61B 5/021* (2013.01); *A61B 5/022* (2013.01); *A61B 5/7257* (2013.01); *A61B 2017/00535* (2013.01); *A61B 2017/00544* (2013.01); *A61B 17/12* (2013.01); *A61B 17/132* (2013.01); *A61B 17/1322* (2013.01); *A61B 17/135* (2013.01); *A61B 2503/06* (2013.01); *A61B 2562/08* (2013.01); *A61H 9/0078* (2013.01)

(58) Field of Classification Search
CPC ............ A61B 2503/06; A61B 2562/08; A61B 5/02141; A61B 5/02233; A61B 90/90; A61B 2017/00119; A61B 17/1355; A61B 5/02; A61B 5/021; A61B 5/022; A61B 17/12; A61B 17/132; A61B 17/1322; A61B 17/135; A61B 2017/00535; A61H 9/0092; A61H 2209/00; A61H 9/0078; G16H 40/63
See application file for complete search history.

(56) References Cited

U.S. PATENT DOCUMENTS

| | | | |
|---|---|---|---|
| 2008/0281241 A1* | 11/2008 | Rowe | A61B 90/98 601/152 |
| 2009/0118628 A1 | 5/2009 | Zhou et al. | |
| 2015/0045679 A1* | 2/2015 | St. Pierre | A61B 5/0225 600/483 |
| 2016/0317051 A1* | 11/2016 | Ashida | A61B 5/02233 |
| 2017/0319420 A1* | 11/2017 | Saggers | A61H 9/0092 |
| 2018/0078158 A1* | 3/2018 | Pekander | A61B 5/02141 |
| 2018/0220908 A1* | 8/2018 | Nomura | A61B 5/022 |

FOREIGN PATENT DOCUMENTS

| | | |
|---|---|---|
| WO | WO-2016004519 A1 | 1/2016 |
| WO | WO-2017037272 A1 | 3/2017 |

OTHER PUBLICATIONS

Huang et al., "Kernel Based Algorithms for Mining Huge Data Sets, Supervised; Semi-Supervised, and Unsupervised Learning", Springer, Studies in Computational Intelligence, vol. 17, 2006 (Year: 2006).*
"European Application Serial No. 21157731.7, Extended European Search Report mailed Apr. 21, 2021", 10 pgs.
"European Application Serial No. 21157731.7, Response to EP Search Report Rule 70a(i) EPC mailed Aug. 23, 2021", 10 pgs.
"European Application Serial No. 21157731.7, Communication Pursuant to Article 94(3) EPC mailed Mar. 5, 2024", 7 pgs.
"European Application Serial No. 21157731.7, Response filed Jul. 5, 2024 to Communication Pursuant to Article 94(3) EPC mailed Mar. 5, 2024", 8 pgs.

* cited by examiner

AUTOMATIC CUFF IDENTIFICATION SYSTEM AND METHOD

CLAIM OF PRIORITY

This application claims the benefit of priority under 35 U.S.C. § 119 (e) of U.S. Provisional Patent Application Ser. No. 62/977,576, filed on Feb. 17, 2020, which is herein incorporated by reference in its entirety.

BACKGROUND

Pneumatic cuffs are used for a variety of medical purposes. The inflatable chamber(s) of pneumatic cuffs allow for application of pressure to patients around appendages for a variety of purposes. For example, pneumatic cuffs are used in conjunction with digital sphygmomanometers to measure patient blood pressure using the oscillometric method. The cuff is inflated to occlude the arterial blood flow, followed by deflation. As the cuff is deflated, the arterial pulsations cause pressure changes in the cuff that are sensed and analyzed to generate information such as mean arterial pressure, systolic pressure, diastolic pressure, and heart rate.

Other pneumatic cuffs are used as tourniquet cuffs, often used in surgical settings, to apply uniform circumferential pressure around a limb or extremity at a desired location. This is done to occlude arterial blood flow following exsanguination to produce a relatively bloodless operative field and to minimize blood loss. Tourniquet cuffs generally include an inflatable chamber, but additionally include a stiffener, contact closures, and a stabilizer. The inflatable chamber holds pressurized gas around the extremity of interest.

Still other pneumatic cuffs, such as deep vein thrombosis (DVT) compression cuffs are used to intermittently apply compression pressure around appendages. This increases blood flow through the deep veins and helps prevent blood clots.

In any case, the pneumatic cuff is generally attached to a console or other monitor of a pneumatic control system that is configured to inflate and deflate the cuff as needed to a particular pressure. But there are a wide variety of pneumatic cuffs, in various types and sizes. The type and size of pneumatic cuff, and the pressure required to treat the patient, can vary on the design, medical procedure, and patient size and medical history. Errors in measurement may occur if an incorrect cuff is attached to the console, which may lead to incorrect pressure application and thereby less effective medical care. Thus, correct selection on the type, size, and brand of pneumatic cuff being used should be verified.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

In the following detailed description of the invention, reference is made to the accompanying drawings that form a part hereof and in which are shown, by way of illustration, specific examples in which the invention can be practiced. These examples are described in sufficient detail to enable those skilled in the art to practice the invention. Other examples can be utilized, and structural, logical, and electrical changes can be made.

Discussed herein is a cuff and console system including a valve for detection of medical cuff type. With any given pneumatic cuff, the pressure curve produced by that pneumatic cuff when inflated depends on the pneumatic resistance in the pathway connecting the pneumatic cuff to the pneumatic control system or device. Discussed herein, placing a valve in the pneumatic pathway between the pneumatic cuff to be placed on a patient and the console in use by a medical professional can alter that resistance. The valve can open at a given threshold pressure, producing a unique pressure curve for each type and size of medical cuff.

A variety of different valves can be integrated with unique pneumatic cuff types so that those pneumatic cuffs produce signature pressure curves identifiable by a processor. Thus, the medical professional can ensure that the cuff being used on the patient is the correct one. For example, the user can verify that the pneumatic cuff being used is the correct brand.

The system and methods discussed herein can allow for cuff identification in pneumatic control systems for medical applications, where the correct cuff type can be automatically selected without substantial reliance on operator diligence, resulting in a higher standard of care. The proposed system and method can allow for the operator to focus on patient care instead of pneumatic cuff type and can eliminate operator error.

The principle of cuff detection uses measurements of pressure and time. Using a one-way, one-time membrane in the pneumatic pathway that opens and remains open after a particular threshold pressure is reached, allows a unique pressure-time curve to be generated. The pressure-time curve can allow for discrimination of cuff type.

The system and methods discussed herein can help eliminate operator error, help the operator of the cuff to perform their role better, and improve the standard of care.

Figure 1:
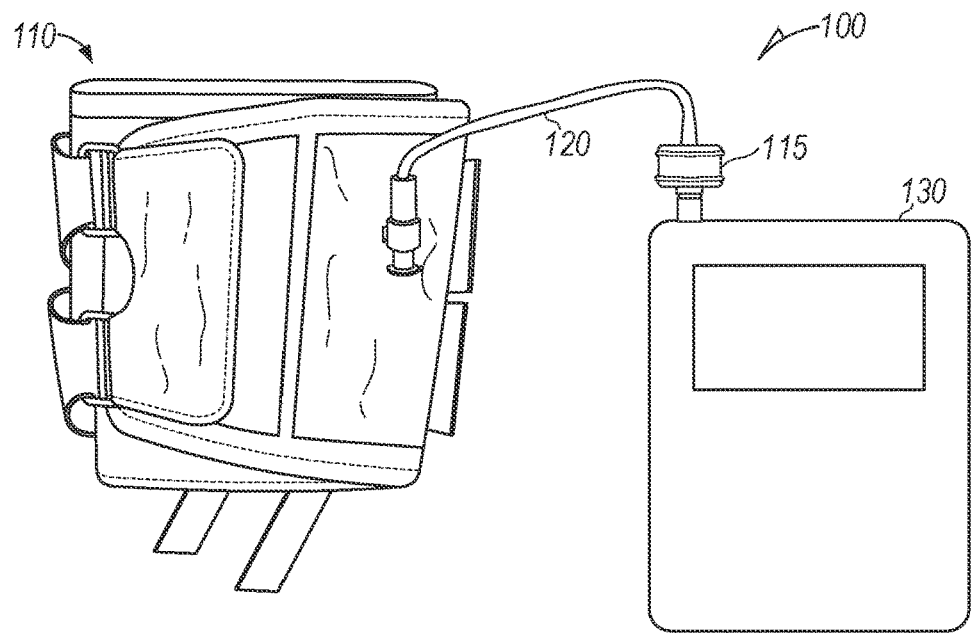
FIG. 1 illustrates a schematic diagram of a cuff system for medical use in accordance with some examples.

FIG. 1 illustrates a schematic diagram of a cuff system 100 for medical use in accordance with some examples. System 100 can include pneumatic cuff 110, pneumatic pathway 120, and console 130.

Pneumatic cuff 110 can be a pneumatic cuff that can, for example, inflate or deflate in a predetermined controlled manner for medical purposes. Pneumatic cuff 110 can be, for example, a tourniquet cuff, DVT (deep vein thrombosis) compression cuff, or a blood pressure cuff. A tourniquet cuff can be used where the medical professional wishes to control arterial and venous blood flow to a portion of an extremity, such as an arm or a leg, for a desired period of time. A DVT compression cuff can be used to prevent blood clots in the deep veins of the leg. Blood pressure cuffs can be used to record blood pressure. Thus, pneumatic cuff 110 can be a cuff designed for a leg, an arm, or other body part. Additionally, pneumatic cuff 110 can be a cuff designed for a child or an adult size, such as a small, medium, or large. In some cases, pneumatic cuff 110 can be different brands. The console 130, discussed below, can help determine and/or verify which kind of pneumatic cuff 110 is attached to the system.

Pneumatic cuff 110 can be made of a sealed inflatable material, such as rubber.

Generally, pneumatic cuff 100 can be of a cylindrical shape with a generally circular cross-section, or alternatively a rectangular shape that can be wrapped around a body part of limb. Pneumatic cuff 100 can have an inflatable cavity or bladder. Pneumatic cuff 110 can have an inlet to connect to pneumatic pathway 120. The inlet can be, for example, a barbed inlet or screw-type inlet that allows direct connection to the inflatable cavity inside the pneumatic cuff 110.

Pneumatic cuff 110 can include an integrated valve 115. Integrated valve 115 can be, for example, a membrane valve, a flap valve, a cross-slit valve, or a Z-shaped valve, as discussed in detail with reference to FIGS. 2, 3A-3B, 4A-4D, and 5A-5D. Integrated valve 115 in pneumatic cuff 110 can be configured to open at or above a specific threshold pressure when pneumatic cuff 110 is inflated. For this reason, when the pressure inside pneumatic cuff 110 is monitored during inflation of pneumatic cuff 110, the resulting pressure versus time curve can be unique to that cuff and valve.

Pneumatic pathway 120 can fluidly connect pneumatic cuff 110 to console 130.

Pneumatic pathway 120 can be an airtight passage, such as tubing or hose, that can be connected and sealed to the pneumatic cuff 110 through an inlet. Pneumatic pathway 120 can have a length sufficient to provide a comfortable amount of spacing between the patient and the user. Pneumatic pathway 120 can be made of one or more sections of hose or tubing; where more than one section of pneumatic pathway 120 is used, they can be connected by an airtight connector, or in some cases, connected by the valve 115 itself. In some examples, valve 115 can be further down pneumatic pathway 120 from pneumatic cuff 110 towards console 130. In other examples, valve 115 can be adjacent an inlet of the pneumatic cuff 110. Fluid, such as air, other gas, or liquid, can travel through pneumatic pathway 120 from console 130 to pneumatic cuff 110 during inflation. In contrast, during deflation, fluid can travel from pneumatic cuff 110 towards console 130 down pneumatic pathway 120.

Console 130 can be connected to the pneumatic cuff 110 through pneumatic pathway 120. Console 130 can include an air-tight hook-up to connect to pneumatic pathway 120. The air-tight hook-up can be, for example, a barbed or angled inlet to which the hose or tubing of pneumatic pathway 120 can be secured. In some cases, the air-tight hook-up can be circular, conical, cylindrical, or otherwise shaped so that it can be inserted over or into an end of pneumatic pathway 120. Console 130 can have a pump, compressor, fan, or other device to inflate pneumatic cuff 110 through pneumatic pathway 120. Console 130 can also include a mechanism through which to deflate pneumatic cuff 110 through pneumatic pathway 120 and valve 115, such as a type of suction or air release. Console 130 can include one or more pressure sensors to detect pressure in the pneumatic cuff 110 and/or pneumatic pathway 120.

Console 130 can be a computing system including a processor and memory including instructions. The processor can be coupled to the memory (e.g., in the console 130). The processor can be used to initiate or evaluate actions in the console 130. An example computing system for console 130, including an example processor and memory, are discussed in more detail with reference to FIG. 9 below.

When executed, the processor can inflate pneumatic cuff 110 for a pre-determined time through pneumatic pathway 120 and valve 115 integrated with pneumatic cuff 110, to a pre-determined pressure. The console 130 processor can inflate pneumatic cuff 110 past the pre-determined threshold pressure so that integrated valve 115 opens. During inflation, pressure sensors can record the pressure in the system (e.g., in pneumatic cuff 110 and/or pneumatic pathway 120) over time. It can be appreciated that the measured pressure values will depend upon the degree of fluid flow restriction caused by the resistance in the pneumatic pathway, which can be made unique to a pneumatic cuff type, thereby allowing cuff type differentiation via unique pressure-time curves. The processor can compare the measured pressure values to reference values that are stored in the memory in a pre-determined lookup table to determine a match for the desired pneumatic cuff type.

The comparison may entail computation of mathematical models to describe cuff types. For instance, the "polynomial least squares" statistical approach can be leveraged for finding the coefficients of polynomial equations that are a "best fit" to a set of X, Y data (pressure and time in this case). The said coefficients can be computed by the processor for the input sensor data and compared to reference values in a predetermined look-up table stored in the memory. Such a comparison can, for example, include computing maximum, minimum, and mean ratios or differences and determining if they are within or outside a pre-determined threshold range to minimize misidentification instances. Alternatively, the processor can look for a specific change in pressure unique to the step-like pressure curve produced by a pneumatic cuff with a valve. In this case, the processor could identify and verify a difference in pressure at a particular time window when the step associated with the opening on the valve would be expected. Although a simple threshold comparison method can be used to identify a cuff type, it may lead to false positives or false negatives in some situations, as it fails to account for any temporal and magnitude deformations in the data resulting from noise and external phenomena such as power instability, temperature changes, etc., that introduce variability in the waveforms or patterns to be matched. To make the identification process accurate and reliable, the processor can use different data validation approaches which may include artificial neural networks (ANNs), dimensional reduction methods, instance-based methods, statistical and probabilistic methods, and Bayesian methods. This is discussed in more detail with reference to FIGS. 6A-6C below.

The processor can then determine a recommendation, based on the comparison. For example, the processor can verify whether the pneumatic cuff 110 attached to the console is the desired type of pneumatic cuff, such as if it is the correct brand, size, or type of cuff, based on the corresponding pressure curve generated by the specific pneumatic cuff with integrated valve. The processor can then output this recommendation to the user (e.g., onto a display). The console 130 can have a housing with a screen or light indicator for conveying this determination to the user. The output can, for example, include using the processor or the display to indicate an error or a verification of the pneumatic cuff type.

Figure 2:
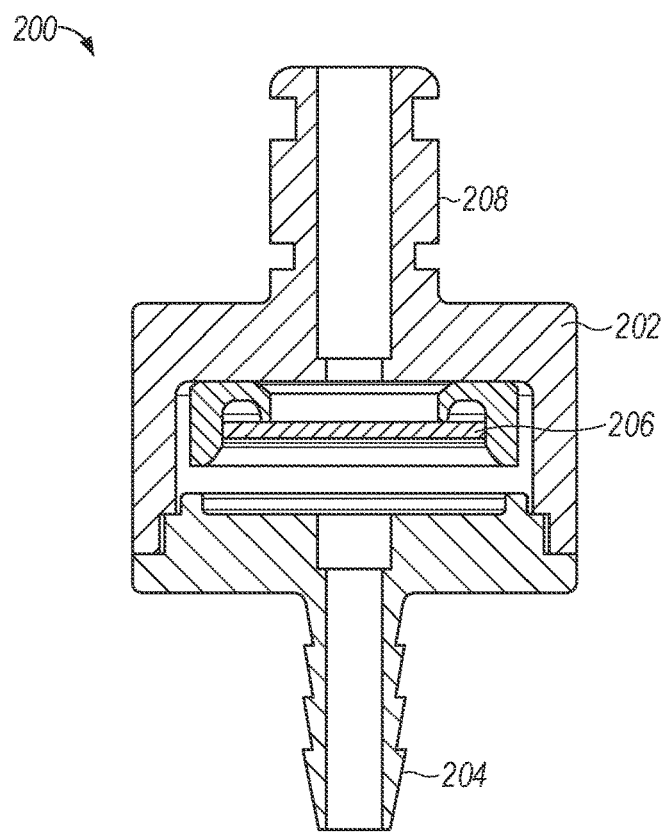
FIG. 2 illustrates a schematic diagram of a valve for use in a cuff system in accordance with some examples.

FIG. 2 illustrates a schematic diagram of a valve 200 for use in a cuff system in accordance with some examples. Valve 200 can include housing 202, pneumatic cuff end 204 for connection to a pneumatic tube/hose, membrane 206, and console end or pneumatic device end 208. Valve 200, when attached to a pneumatic cuff and inflation of that pneumatic cuff is occurring, fluid flows from console end 208 through membrane 206 and out of pneumatic cuff end 204.

Housing 202 can enclose valve 200 and allow valve 200 to remain an airtight passage between a console and a pneumatic device.

Console end 208 can connect to a console (e.g., console 130 of FIG. 1) including a processor and memory capable of inflating a pneumatic cuff and determining whether the correct pneumatic cuff is attached based on the comparison of pressure curves.

Membrane 206 can be disposed inside housing 202, separating pneumatic cuff end 204 from pneumatic device end or console end 208. Membrane 206 can open when a threshold pressure is reached inside valve 200. Generally, this can occur when fluid is inputted from pneumatic device end or console end 208 towards pneumatic cuff 204, i.e., during inflation, at a pressure at or above the threshold pressure.

Pneumatic device end or console end 208 can connect to a pneumatic cuff (e.g., pneumatic cuff 110 of FIG. 1) for medical applications.

When valve 200 is integrated with a pneumatic cuff and the pneumatic cuff is inflated, a unique step-like pressure curve can be generated once the threshold pressure is reached and the membrane 206 is forced open, as discussed with reference to FIG. 1 above.

Figure 3A:
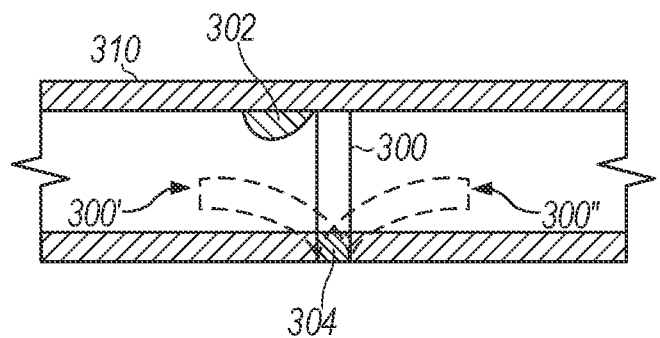
FIGS. 3A-3B illustrate schematic diagrams of a flap valve for use in a cuff system in accordance with some examples.
Figure 3B:
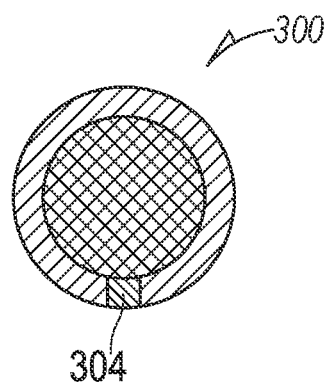

FIGS. 3A-3B illustrate schematic diagrams of a flap valve 300 with pressure bump 302 for use in a cuff system in accordance with some examples. FIG. 3A shows flap valve 300 with anchor 304 in an air-tight pneumatic pathway 310 from a side view, in open positions 300' and 300" (shown in broken lines) and closed position 300. FIG. 3B shows flap valve 300 from a frontal view.

Flap valve 300 is an example of a bi-directional valve for use with a pneumatic cuff to generate a unique pressure curve and allow for identification of cuff type. A bi-directional valve, such as flap valve 300, can be strategically placed in the pneumatic pathway 310 between the pneumatic cuff and the user console. The bi-directional valve can be integrated with the pneumatic cuff. The valve 300 can be anchored in the pneumatic pathway 310 or at the entrance of the pneumatic cuff with an anchor 304.

Flap valve 300 can open circumferentially. Flap valve 300 can have a cross-section with a fixed area. Flap valve 300 can be disposed in pneumatic pathway 310 adjacent pressure bump 302. Pressure bump 302 can be a micro-bump or other shape that holds flap valve 300 in a closed position until fluid with a specific threshold pressure pushes flap valve 300 into an open position 300'. In contrast, when valve 300 is deflating, the valve can be in open position 300". As the valve 300 moves from inflation to deflation, the valve 300 can face slight resistance from the micro-bump 302 before completely opening to position 300". This slight resistance can be a fraction of the resistance seen overall during inflation. The pre-determined threshold pressure can be applied to overcome the resistance due to pressure bump 302 and open flap valve 310.

When pressure is applied to the pneumatic pathway by use of a fluid, the pressure in that pneumatic cuff and/or pneumatic pathway can be recorded over time to produce a pressure-time curve unique to the pneumatic pathway containing the flap valve 300 with pressure bump 302. In case of the flap valve 310, the pre-determined threshold pressure must be reached in order to overcome the resistance due to the pressure bump 302 and move the valve 310 from closed position 300 to open position 300'. A processor, such as the one discussed with reference to FIG. 1, can produce a pressure-time curve for identifying the attached cuff based on measurements by a pressure sensor monitoring the pneumatic passageway pressure.

Figure 4A:
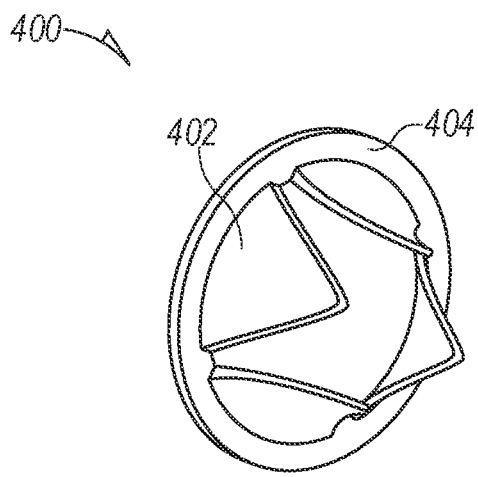
FIGS. 4A-4C illustrates schematic diagrams of a cross-slit valve for use in a cuff system in accordance with some examples.
Figure 4B:
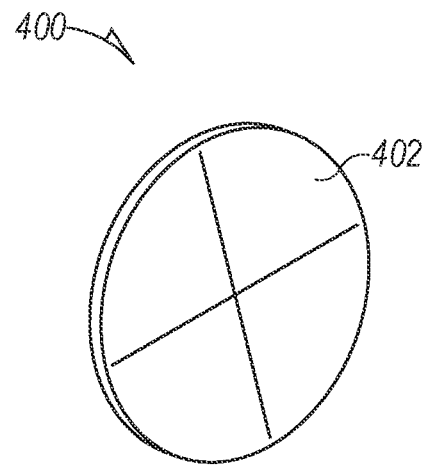
Figure 4C:
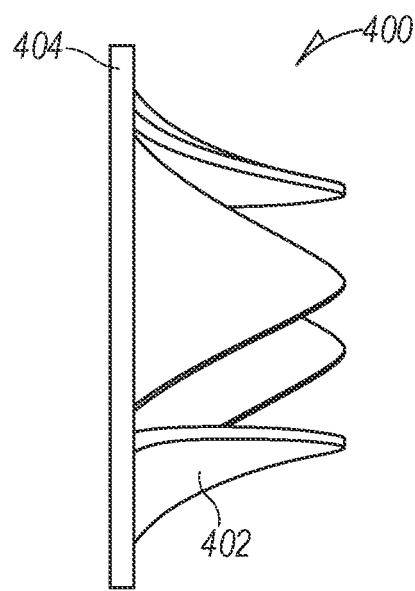

FIGS. 4A-4C illustrate schematic diagrams of a cross-slit valve 400 for use in a cuff system in accordance with some examples. Cross-slit valve 400 includes flaps 402 and frame 404. FIGS. 4A and 4C show cross-slit valve 400 in an open position 400', when the pneumatic cuff is inflated. FIG. 4B shows cross-slit valve 400 in a closed position, when there is no inflation (e.g., deflation).

Cross-slit valve 400 is supported by frame 404 that can be assembled inside a pneumatic pathway or pneumatic valve. Frame 404 can be, for example, plastic, and can be a snap-fit, friction-fit, or other mechanically fastened frame that holds cross-slit valve 400 in place in the pneumatic pathway, allowing for airtight flow.

Cross-slit type valve 400 can also be a type of bidirectional valve that works in a similar way to flap valve 300, except that the predetermined pressure difference required to open the valve can be created by lips 402 of cross-slit valve 400 being in contact with each other instead of the pressure bump 302 in the flap valve 300. Lips 402 of the cross-slit valve 400 can open when the pre-determined threshold pressure difference is achieved. Similar to the valves discussed with reference to FIG. 2 and FIGS. 3A-3B, the cross-slit type valve 400 can produce a stepped pressure curve. Cross-slit type valve 400 can be designed to be in a predisposed open position such that it offers zero to minimal resistance during deflation.

Figure 5A:
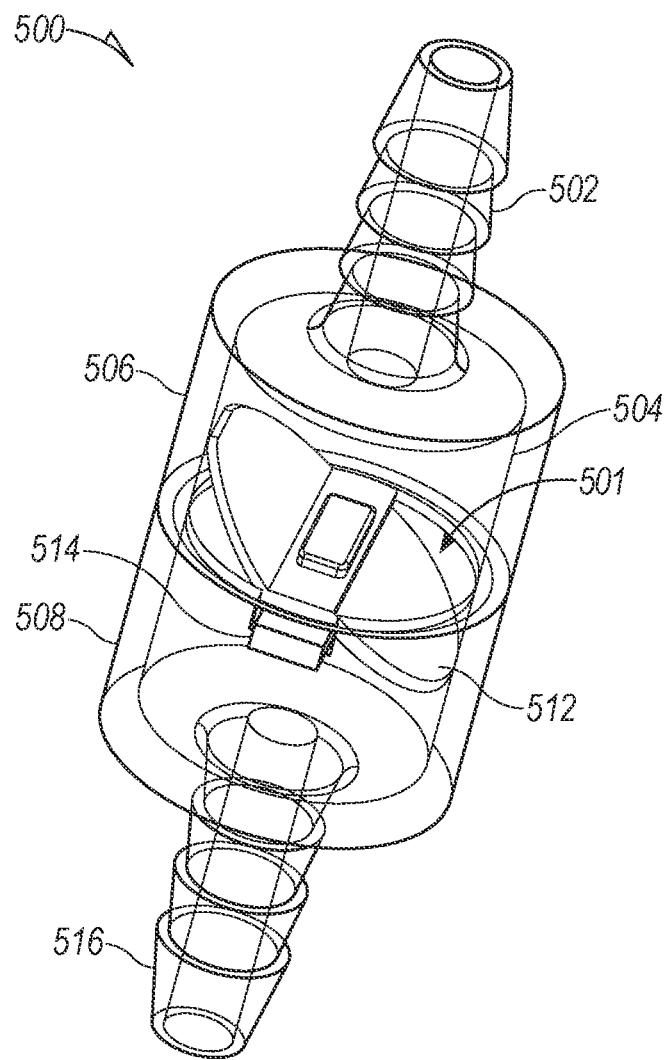
FIGS. 5A-5D illustrates various views and schematics of a Z-valve for use in a cuff system in accordance with some examples.
Figure 5B:
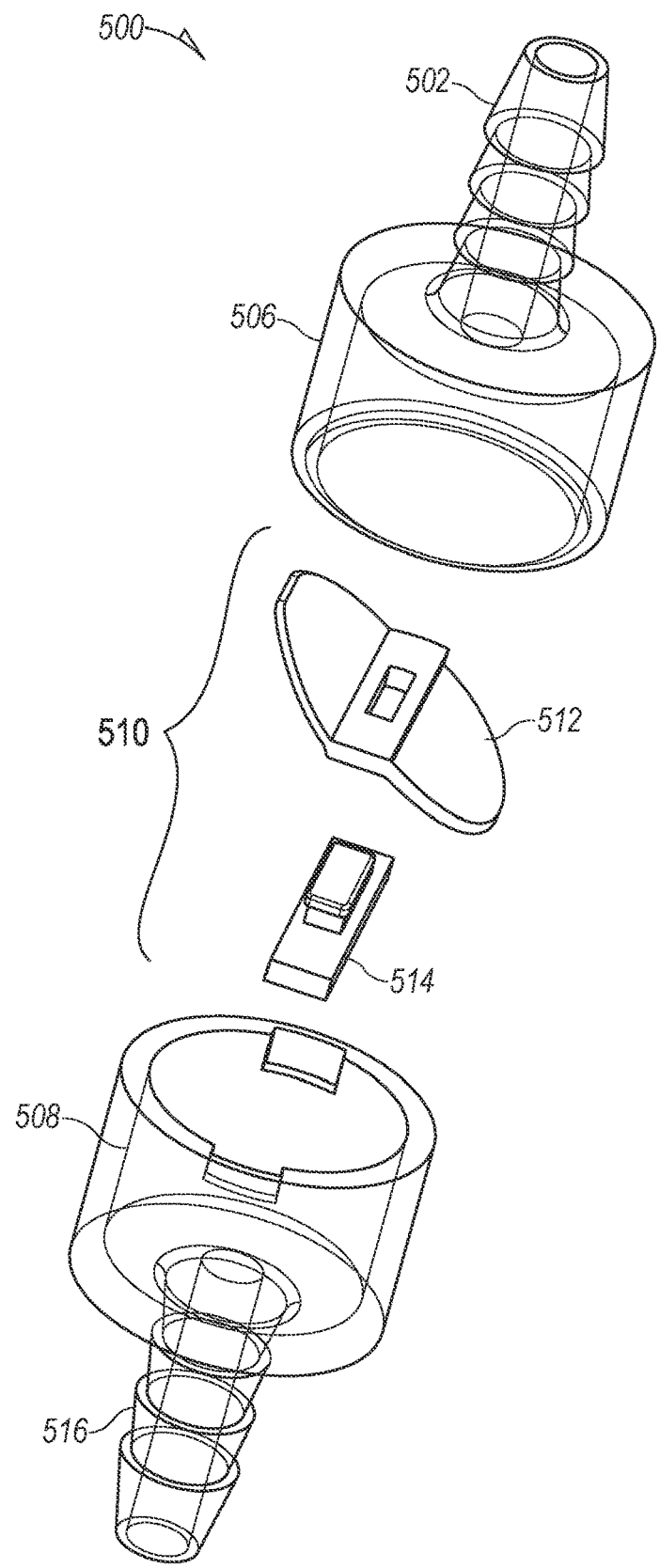
Figure 5C:
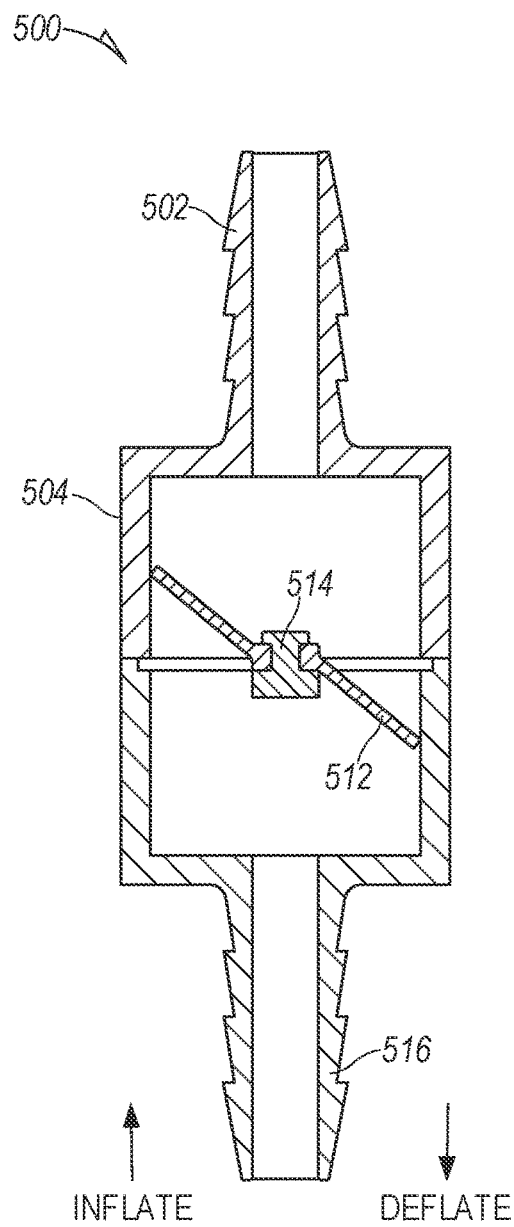
Figure 5D:
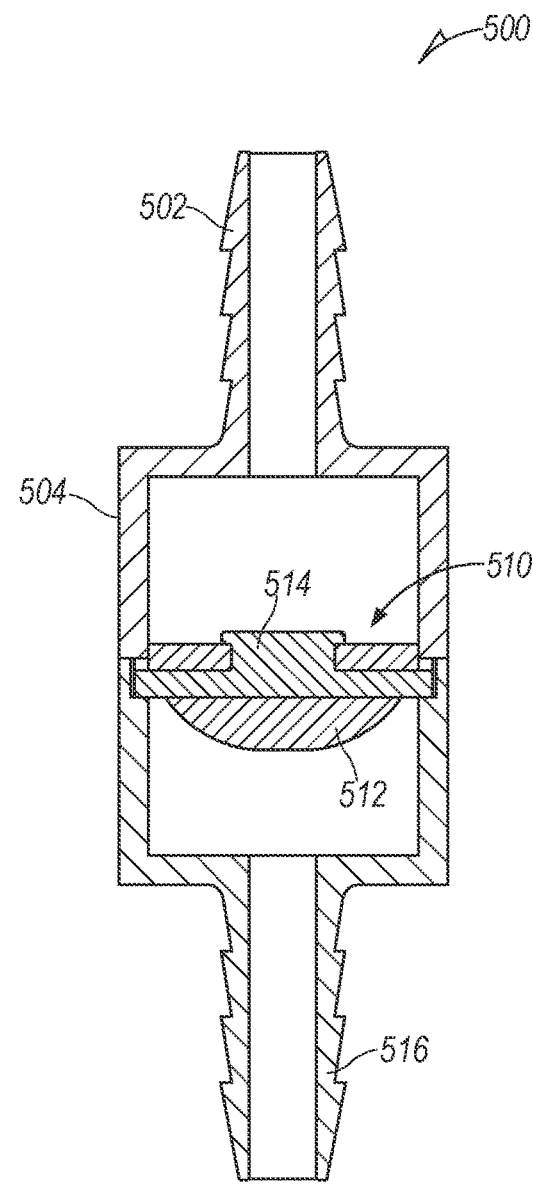

FIGS. 5A-5D illustrate various views and schematics of a Z-valve assembly 500 for use in a pneumatic cuff system in accordance with some examples. FIG. 5B shows a perspective view of Z-valve assembly 500, and FIG. 5B shows an exploded perspective view of Z-valve assembly 500. FIGS. 5C and 5D show cross sectional views of Z-valve assembly 500 in open and closed positions. FIGS. 5A-5D will be discussed together.

Z-valve assembly 500 can include first end 502, connector 504 with pieces 506, 508, Z-valve subassembly 510 with valve 512 and support member 514, and second end 516.

First end 502 and second end 516 can be barbed ends that connect to a pneumatic pathway and/or pneumatic cuff and console.

Connector 504 can be a housing piece that encloses Z-valve subassembly 510.

Connector 504 can be made of two pieces 506, 508, which can be top and bottom halves of the assembly. Pieces 506, 508, can be ultrasonically welded together to create an airtight passage between first end 502 and second end 516.

Z-valve subassembly 510 can be made of two pieces, support member 514 and valve part 512. Support member 514 can allow for anchoring and centering of valve part 512. Support member 514 can be ultrasonically welded to bottom half 508 of connector 504.

Valve part 512 can be an elastomeric valve. In some cases, valve part 512 can include two "flaps," one on either side of support member 514, each flap can move independently. For example, valve 500 can be a combination of two angled flap valves in subassembly 510. One flap can open during inflation, while the other can open during deflation. The former can remain closed during deflation because it rests on the wall of two-way barbed connector 504, which can form a seal. Similarly, the latter can remain closed during inflation, and can be designed such that it offers minimum resistance during deflation (e.g., it can be designed to be normally partially open).

Z-valve assembly 500 can interface with a pneumatic cuff and console at the barbed ends 502, 516, creating an airtight passage when hoses or tubing are attached. The connection can be able to withstand pressures generated during blood pressure monitoring or tourniquet operation, depending on the type of pneumatic cuff used.

When a pneumatic cuff is being inflated through Z-valve assembly 500, fluid can flow from a console into first side 502, through connector 504 and Z-valve sub-assembly 510, and out second side 516 to the pneumatic cuff. As discussed above with reference to FIG. 1, a processor in the console can record a pressure curve during inflation of the pneumatic cuff and/or pneumatic pathway containing Z-valve assembly 500.

Figure 6A:
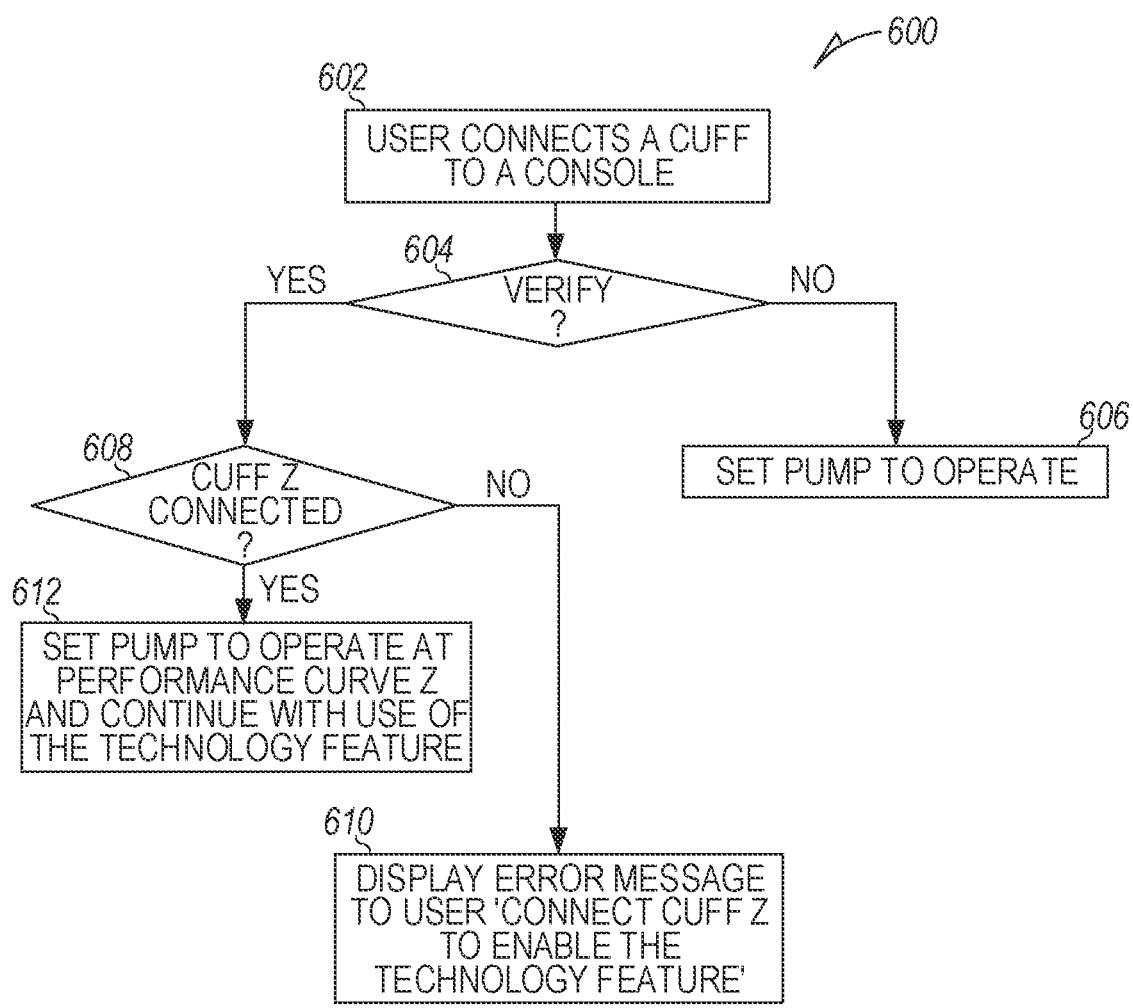
FIGS. 6A-6C illustrate flow charts depicting a method of detecting the type of cuff used in a medical application in accordance with some examples.

FIG. 6A illustrates a flow chart depicting a method 600 of detecting the type of cuff used in a medical application in accordance with some examples. In method 600, the type of medical pneumatic cuff used can be detected using pressure curve measurements.

First, at 602, the user can connect a pneumatic cuff to a console. Next, the user can be prompted whether or not they wish to verify the type of pneumatic cuff attached at 604. If verification is not required or needed, the console can continue to operate without verification at 606.

If the pneumatic cuff needs to be verified, the console can then confirm that the physical connection between the pneumatic cuff and the console is correct at 608. If the pneumatic cuff is not connected correctly, the console can display an error message on the console screen or indicate an error through a light or other visual or audible source at 610.

If the pneumatic cuff is correctly attached, the console can initiate inflation and recordation of a pressure curve at 608. In this case, the console can inflate the pneumatic cuff at a pre-determined pressure for a set amount of time. Pressure sensors in the console can record the pressure in the pneumatic cuff and/or pathway over that time in a console memory. A processor, such as a data acquisition system (DAS or DAQ), in the console can sample the measured analog sensor signal and convert the resulting samples into digital numeric values that can be manipulated by the processor.

The processor can, for example, conduct a similarity search in a sequence database. In this example, the processor can determine similarity between two time series or sequences of equal length, $\vec{x}=(x\_0, x\_1, \ldots, x\_(n-1))$ and $\vec{y}=(y\_0, y\_1, \ldots, y\_(n-1))$ by computing a similarity measurement such as the Euclidean Distance $D(\vec{x}, \vec{y})$ given by Equation (1) below.

$$D(\vec{x}, \vec{y}) = \left( \sum_{i=0}^{n-1} |y_i - x_i|^2 \right)^{\frac{1}{2}} \quad (1)$$

The time sequences $\vec{x}$ and $\vec{y}$ are then said to be similar if $D(\vec{x}, \vec{y}) \le \epsilon$, where $\epsilon$ is a pre-determined threshold, and can be selected based on the need of the application. To account for vertical shifts between the sequences, the said two sequences can said to be similar, given a pre-determined threshold ($\epsilon$) if Equation (2) holds true. This model allows for better estimation of similarity when similar trends are running at two completely different levels.

$$D(\vec{x}, \vec{y}) = \left( \sum_{i=0}^{n-1} ((y_i - x_i) - (y_A - x_A))^2 \right)^{\frac{1}{2}} \le \epsilon \quad (2)$$

where $$x_A = \frac{1}{n}\sum_{i=0}^{n-1} x_i \text{ and } y_A = \frac{1}{n}\sum_{i=0}^{n-1} y_i \quad (3)$$

Figure 6B:
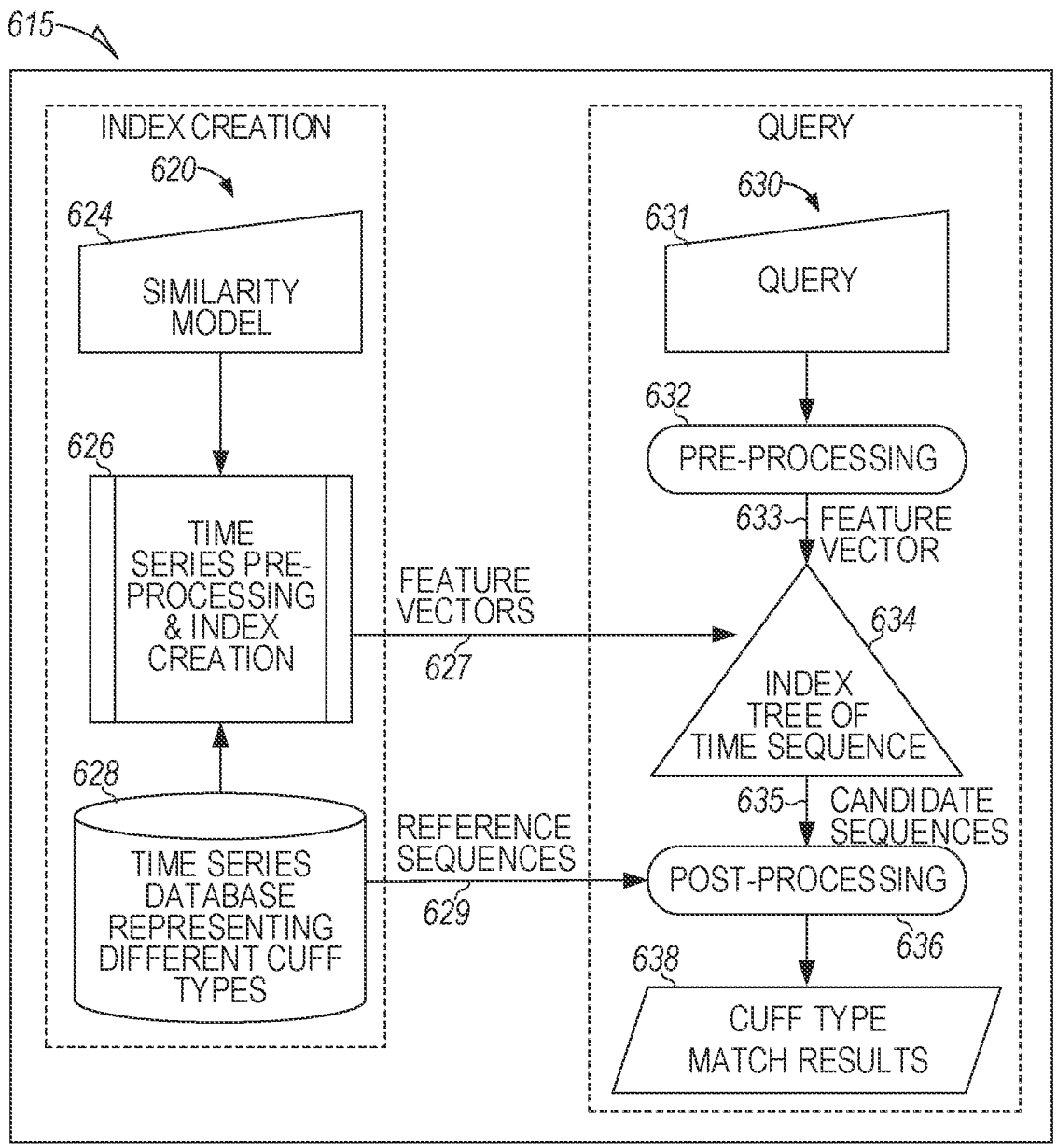

Time series indexing 615 can be employed to support efficient retrieval and matching, using such similarity models, as depicted in FIG. 6B. In time series indexing method 615, after pre-processing 626 of time series, which may include normalization, transformation, noise reduction, etc., a set of feature vectors 627 can be produced and indexed in index creation method 620. Discrete Fourier Transform (DFT) can be used to map the signal from time domain to a feature space of low dimensionality such as frequency domain. DFT can preserve the Euclidean distance so that no qualified sequence will be rejected, thereby assuring no false dismissal. The power concentration of the transformed sequence can be concentrated on as few coefficients as possible, so that they are sufficient to differentiate between two sequences.

These feature vectors 627 can then be inserted into a multi-dimensional index tree 634 using methods such as the R-Tree, on which the query 630 can be raised. Upon query 631 arrival, pre-processing 632 can be done in the same way as for the time series database 628 in index creation. The produced feature vector 633 can be matched against the index tree 634, which can result in a candidate sequence 635, if found. Non-qualified sequences and false alarms can be filtered in the post-processing step 636, by matching with the query sequence in the time domain using full dimension. The cuff type match results 638 can then be outputted for further decision making.

To account for time shifts in sequences, similarity search under time wrapping can be utilized. Two additional steps can be leveraged in creating a time series database that supports time wrapping. First, in the index creation/pre-processing step 632, 634, K-L transform can be applied to map the original sequence to lower dimension feature vectors. Then, the multi-dimensional index can be built, and a filtering function can be used to prune away false alarms from the candidate sequences in the post-processing step.

Alternatively, Discrete Wavelet Transform (DWT) can be used instead of DFT. DWT is a multi-resolution representation of signals and has the time-frequency localization property. For application to pneumatic cuff identification, a wavelet representation of a pressure signal can identify at what time and frequency a particular pressure event occurred.

For example, Haar Wavelet Transform (a type of DWT) can be employed, which uses the Haar Wavelet method, defined by Equation (4) below. The Haar Wavelet method can be used in order to reduce storage required for sequences and reduce computing time. The Haar Wavelet method can allow for good approximation with a subset of coefficients, preserves Euclidean distance, and can be computed quickly and easily.

$$\omega_i^j(x) = \psi(2^j x - i) \; i = 0, \ldots, 2^j - 1 \qquad (4)$$

where $$\psi(t) = \begin{cases} -1 & 0 < t < 0.5 \\ -1 & 0.5 < t < 1 \\ 0 & \text{otherwise} \end{cases} \qquad (5)$$

together with a scaling function $$\psi(t) = \begin{cases} 1 & 0 < t < 1 \\ 0 & \text{otherwise} \end{cases} \qquad (6)$$

With the use of DWT, such as the Haar Wavelet Transform, pre-processing can be used to extract the feature vectors with reduced dimensionality. Those feature vectors can be used to build the index before querying is performed.

After the index is built, a content-based search can be performed using 'range querying' and 'n nearest neighbor querying'. For range queries, similar sequences with distance ≤ε from the query can be looked up in the index and returned. Then, a post-processing step can be applied to these sequences to obtain actual distance in time domain to remove all false alarms.

For n nearest queries, the n nearest neighbors of query $\vec{q}$ in the index can be found. The Euclidean distances in time domain can be computed between the query sequence and all n nearest neighbors obtained, which are $D(\vec{q}, \vec{nn}_i^1)$, where $\vec{nn}_i^1$ is the nearest neighbor i (1≤i≤n), with $\vec{nn}_n^1$ farthest from the query $\vec{q}$. Then, a range query evaluation can be done on the same index by setting $D(\vec{q}, \vec{nn}_i^1) = \epsilon$ initially. A list of n nearest sequences $\vec{nn}_i^2$ can be found and their Euclidean distances will be kept, obviating the need for a post-processing step.

In some cases, the user can indicate on the console which specific type of pneumatic cuff should be connected. For example, the user can indicate, through a button or touch screen user interface, that a blood pressure cuff of a medium adult size and brand Z should be attached. In this case, the processor can retrieve the pressure curve associated with this particular type of pneumatic cuff from the library of pressure curves stored in the memory of the console. The processor can then mathematically compare the generated pressure curve to the store pressure curve.

Figure 6C:
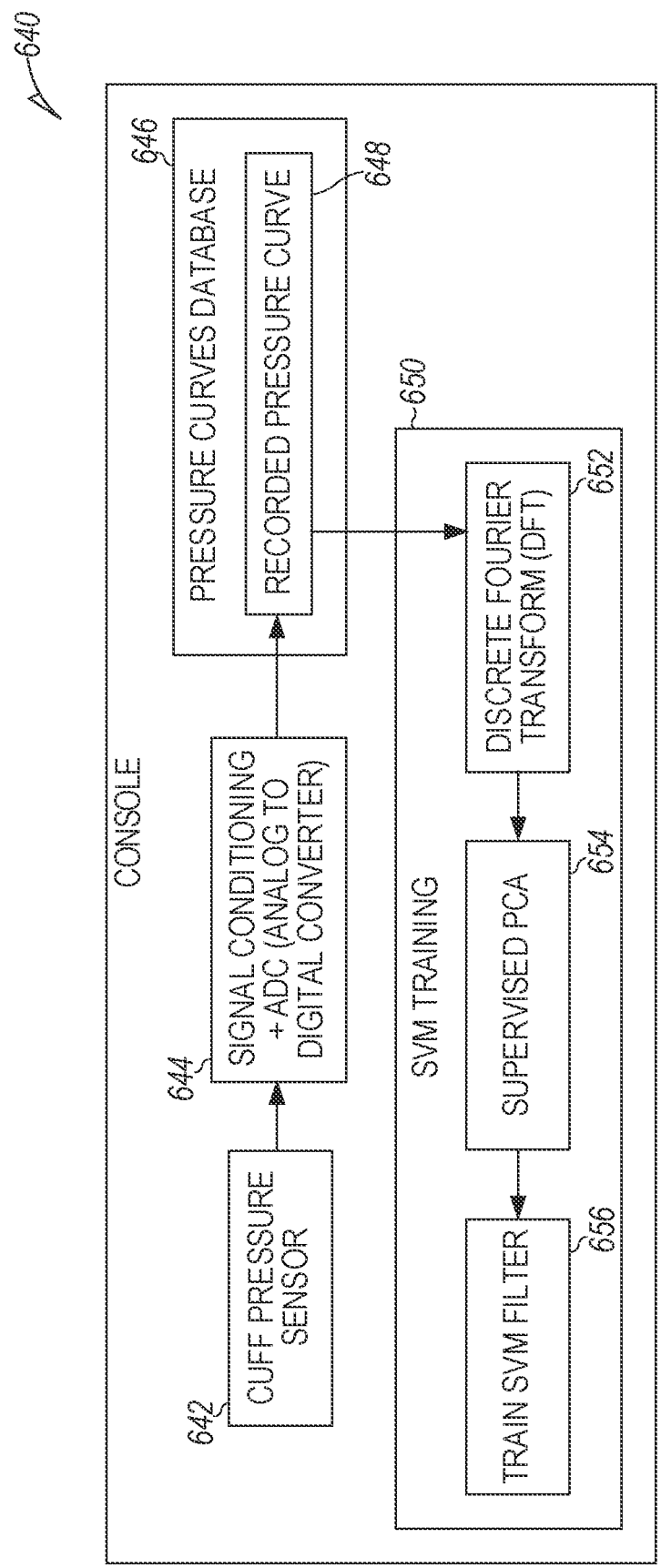

For this analysis, a neutral network algorithm can be used such as shown in FIG. 6C, which is a schematic of Support Vector Machine (SVM) training. For example, if the user indicates on the console that a particular brand Z cuff is desired, the goal is then to differentiate between a "correct cuff" and an "incorrect cuff." In this case, the "correct cuff" would be the Z brand cuff.

For this analysis, a neural network algorithm 640, such as a Support Vector Machine (SVM) can be used. An SVM is a binary classifier that requires a low number of samples. The sensor output from the cuff pressure sensor 642 can be first converted into digital signals which can be pre-processed to remove random noise, power line interference, and correct any baseline wander in signal conditioning step 644. The pre-processing may include normalization, transformation, etc., as discussed before Several signals can be recorded to form a database for SVM training, after which the best feature to form a classifier for cuff recognition can be selected.

Specifically, this can be accomplished by first setting up a database of multiple different pressure curves corresponding to different pneumatic cuff types via experimentation, such as shown in pressure curves database 646. Then, supervised principal component analysis (PCA) 654 and independent component analysis (ICA) can be used to generate and select characteristic features of those pressure curves. PCA 654 can be used to generate mutually uncorrelated features while packing relevant information into several eigenvectors. Subsequently, SVM training 650 can be used to derive an SVM classifier 656.

A set of eigenvectors can be computed from the training data, and some of the eigenvectors can be selected for classification according to the corresponding eigenvalues or according to binary classification capability. The eigenvectors can effectively carry feature information required for distinguishing between two classes.

For example, if there are two sets of training samples: A and B, with N sample each. $\Phi_i$ represents each eigenvector produced through PCA. These 2N training samples can be projected onto an axis extended by the corresponding eigenvector and those eigenvectors that have more signal information can be selected. The mapping result can be defined as $\lambda_{i,j}$ (1≤i≤M; 1≤j≤2N). M is the number of eigenvectors and 2N is the total number of training samples. A classifier $f_i$ can be trained using neural network and can be used to separate $\lambda_{i,j}$ into two groups: a correct cuff and an incorrect cuff, with a minimum error $E(f_i)$. If $E(f_i)$ is ≤ε (a predetermined threshold), select this eigenvector from the original set. These selected eigenvectors can be represented back to signal data representing a typical pressure. The ICA can then be used to find a group of independent components that explain the data. ICA accounts for higher order statistics and thus provides more powerful data expression than PCA. The output of ICA, represented by $\overline{A}$ and $\overline{B}$, can be then selected as training inputs for the SVM process.

In the SVM training process, the data represented by $\overline{A}$ and $\overline{B}$ can be mapped into a feature space F via a non-linear mapping $\Phi$, and linear regression can be performed in this space. It is assumed that inputs vectors are $\overline{X}_1, \overline{X}_2, \ldots, \overline{X}_N$ and that $z_i \in \{1, -1\}$ is the class label of $\overline{X}_i$.

$$f(\overline{X}) = (\omega, \Phi(\overline{X})) + b \; (\Phi: R^3 \to F, \omega \in F). \qquad (7)$$

Thus, linear regression in the feature space can correspond to nonlinear regression in the low-dimensional input space $R^3$. b is the threshold and the dot product has to be computed, for which a kernel function defined by Equation (8) that satisfies the Mercer's condition is used so the dot product can be implicitly expressed in the low-dimensional input space.

$$K(\overline{X}_i, \overline{X}_j) = \Phi(\overline{X}_i)^T \Phi(\overline{X}_j) \qquad (8)$$

Now, the following equation can be solved:

$$\max \cdot \overline{\omega}(\alpha) = \sum_{i=1}^{n} \alpha_i - \frac{1}{2} \sum_{i=1,j=1}^{n} \alpha_i \alpha_j z_i z_j K(\overline{X}_i, \overline{X}_j) \quad (9)$$

$$\text{subject to } \xi \geq \alpha_i \geq 0; \sum_{i=1}^{n} \alpha_i z_i = 0$$

where $\xi$ is a tradeoff parameter between error and margin and $\alpha_i$ are Lagrangian multipliers.

Alternatively, the processor can receive the pressure data and generate a pressure curve and compare the generated pressure curve to a whole library of pressure curves, or to a sub-set of pressure curves. In this case, for example, a pressure curve can be generated for a pneumatic cuff of a particular brand B. The user can indicate on the console that brand B is desired. The processor can retrieve all stored pressure curves associated with brand B of pneumatic cuffs. The processor can then compare the generated pressure curve to the retrieved pressure curves, until the processor finds a retrieved pressure curve which, when compared to the generated pressure curve, has a mathematical fit. In an alternative case, the user could simply indicate that a generic pneumatic cuff is to be tested, and processor could inflate the pneumatic cuff, which can be monitored by pressure sensors. The processor can then produce a pressure curve associated with the attached cuff. The processor can subsequently or simultaneously compare the produce pressure curve with a library of pressure curves and suggest to the user which type of pneumatic cuff is attached through a display.

In any case, the determination by the processor can then be conveyed to the user. In some cases, the verification of the cuff type can be conveyed through a screen on the console. In this case, the processor can, for example, display the brand, size, and/or type of the pneumatic cuff which most closely matches the generated pressure curve on the screen. Alternatively, where a specific pneumatic cuff brand, size, and/or type was inputted by the user, the processor can display a simpler code such as "verified" or "correct" to affirm that the desired pneumatic cuff is attached. In other cases, the verification can be conveyed to the user via a small light, such as an LED light, on the console. In other cases, the verification can be conveyed to the user via a sound or tone.

Once the type of cuff is verified by the console and the user confirms, the user can then proceed to provide medical assistance to the patient using the correct pneumatic cuff. In this case, the console can adjust the pressure of inflation depending on the particular cuff being used.

For example, where a tourniquet cuff is being used, the user can first initiate the verification process. The console can inflate the tourniquet cuff at a specific test pressure near the range of the threshold pressure for the integrated valve. The console can sense and record the pressure curve for that inflation. Then, the processor in the console can compare the generated pressure curve to a library of pressure curves; specifically, to pressure curves associated with the specific type of tourniquet cuff desired. Then the console can indicate to the user that the correct pneumatic cuff is attached or not.

Subsequently, when the user begins to operate the pneumatic cuff system with the patient, the identification of the tourniquet cuff type can allow the processor in the system to choose and correlate a specific inflation pressure for that type of cuff. For example, where a tourniquet cuff is verified, the processor can determine the applicable range of inflation pressures to initiate medical use of the tourniquet cuff at that specific pressure.

For example, a pneumatic compression system or device having a 'synchronized flow technology (SFT)' feature mode is designed to be used with a specific cuff design or type, to offer advanced treatment sequences effective in deep vein thrombosis (DVT) prevention. This patient specific SFT Mode can use an internal sensor to apply pressure in sync with respiratory-related changes in venous phasic flow to optimize peak venous velocity at lower applied pressures, thus improving patient outcomes.

In such a scenario, the correct cuff type would be needed, for example, the corresponding SFT cuff. The system software can be programmed such that only upon identification of the desired SFT cuff, the SFT mode is enabled. The system can still, for example, have the capability to operate in Regular Mode if a Regular cuff type (alternative cuff) is connected.

The SFT cuff can be designed to have a higher pneumatic resistance as compared to a regular or alternative cuff, by placing a valve or a combination of valves in the pneumatic passageway of the SFT cuff. Thus, there would be two distinct system curves, with the head difference between the two system curves being equivalent to the pressure drop across the valve(s) integrated in the pneumatic passageway of the SFT cuff. The SFT cuff would therefore produce a pressure curve distinct from the alternative cuff.

To overcome the pneumatic resistance in the SFT cuff pneumatic pathway, and in order to provide the necessary compression treatment for addressing DVT, the console pumping up the cuff would have to do extra work, thereby increasing the pump head and changing the pump curve to get a different operating point.

This can be achieved, for example, by varying speed driven pumps while ensuring that the pump operates in a preferred region, such as the operating point of the pump, relative to its best efficiency point, remains constant.

The system can, for example, be programmed to supply a higher voltage to increase the pump speed (RPM), thereby increasing the pump head upon detection of the SFT cuff. (Pump head is directly proportional to the square of the pump speed, according to the pump affinity laws). Similarly, the pump can be programmed to operate at a different operating point with reduced RPM for the alternative cuff.

Figure 7:
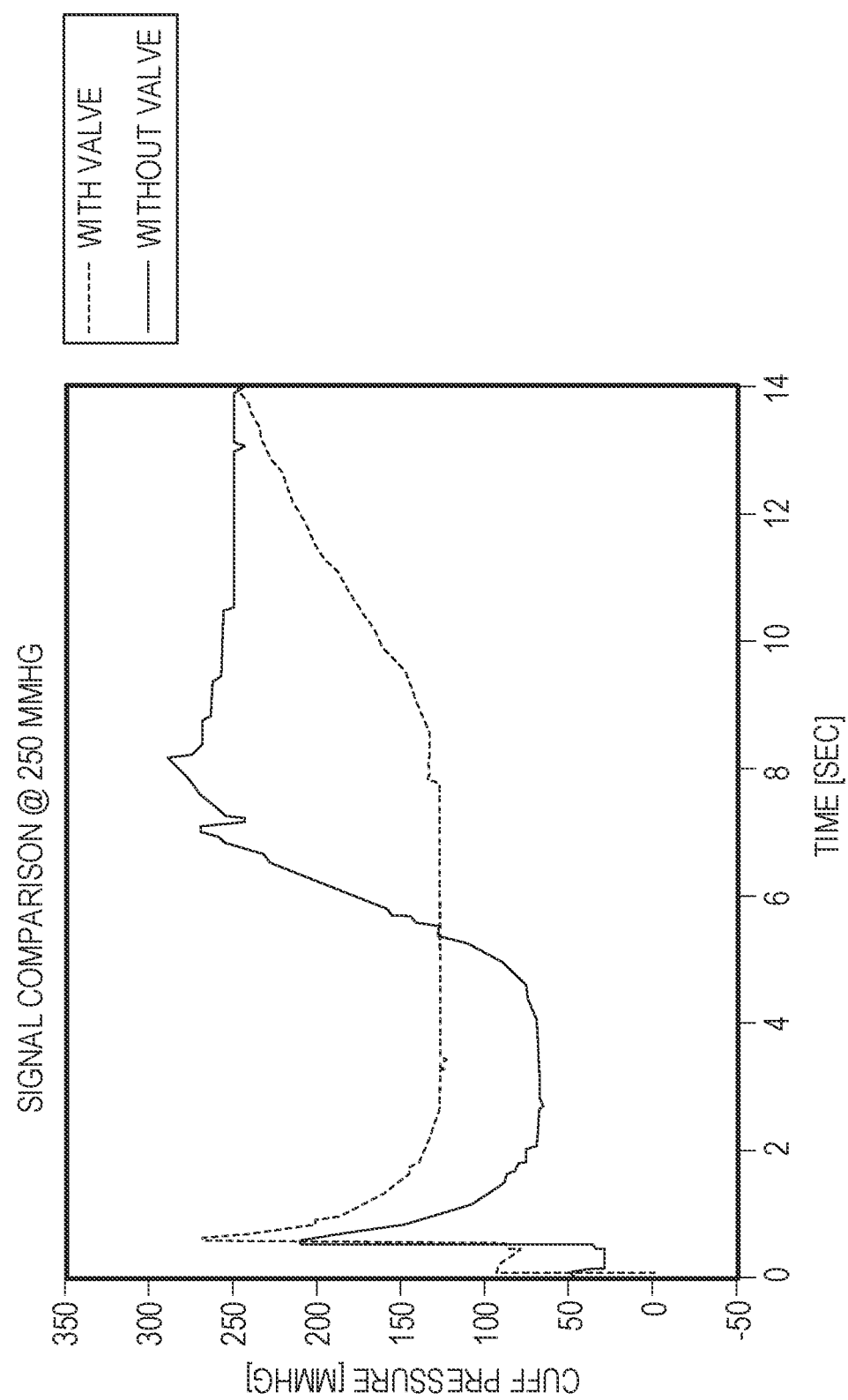
FIG. 7 illustrates pressure curves for cuff systems in accordance with some examples.
Figure 8A:
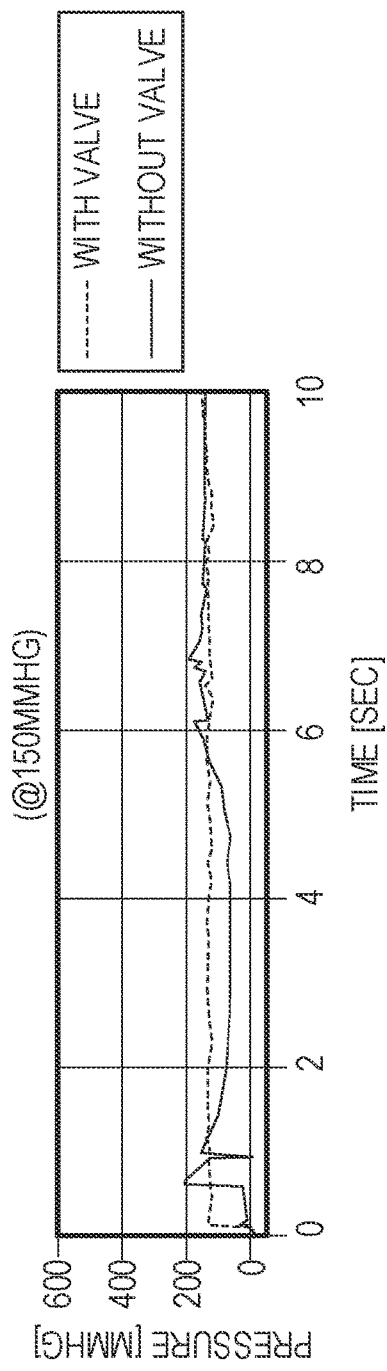
FIGS. 8A-8D illustrate pressure curves at different operating pressures for cuff systems in accordance with some examples.
Figure 8B:
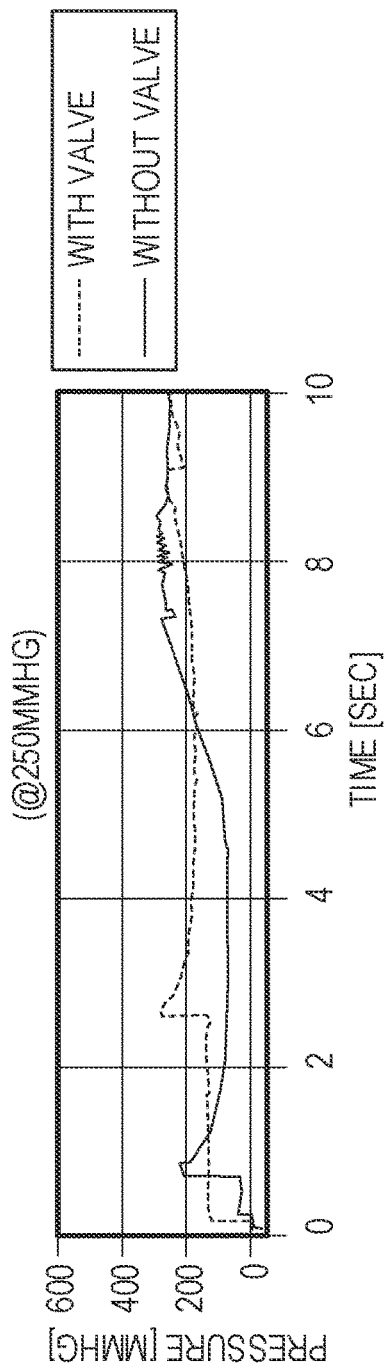
Figure 8C:
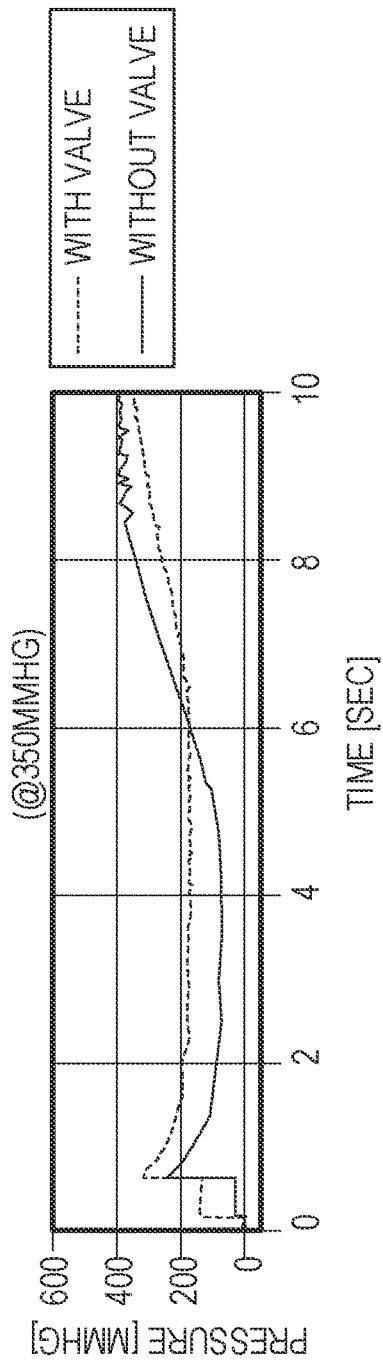
Figure 8D:
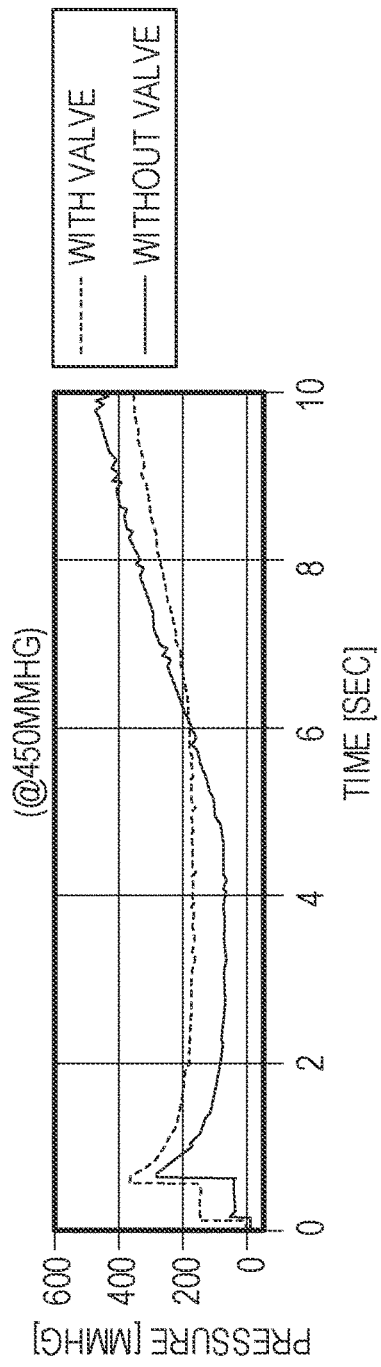

FIGS. 7 and 8A-8D show example pressure curves generated for a pneumatic cuff with an integrated valve. In FIG. 7, a medical pneumatic cuff was inflated over a period of 14 seconds to a set target pressure of 250 mmHg, from a console attached to the pneumatic cuff.

Shown are two pressure curves: one where the pneumatic cuff did not include a valve, and one where the pneumatic cuff did include a valve. The curve generated with the valve has a noticeably different shape than the one without a valve. More specifically, the with-valve curve markedly rises around the 8 second mark from a relatively higher pressure level as compared to the without-valve curve, which markedly rises around the 4 second mark from a relatively lower pressure level. The difference between the said pressure levels is about 50 mmHg, which is equivalent to the threshold pressure differential required to open the valve, i.e, the valve in this case has an opening pressure of about 50 mmHg. In other words, the pneumatic pathway resistance increases by an amount equal to the opening pressure of the valve. Due to this reason, it takes a little longer for the with-valve curve to start appreciating to the set target pressure of 250 mmHg.

Similarly, FIGS. 8A-8D show a series of pressure curves for pneumatic cuffs inflated over 10 seconds. FIGS. 8A-8D show inflation at increasing pressures of 150 mm Hg, 250 mm Hg, 350 mm Hg, and 450 mm Hg, respectively. FIGS. 8A-8D each show one pressure curve without a valve, and one pressure curve with a valve. All the curves shown in FIGS. 8A-8D used the same pneumatic cuff type and size.

The pressure curves in FIGS. 8A-8D show a pattern. The pressure curves generated at pressures of 150 mm Hg, 250 mm Hg, 350 mm Hg, and 450 mm Hg, with the valve, stayed at a more constant average higher pressure after the first few seconds due to the presence of the valve. These curves differed from the pressure curves generated without valves in that the pressure curves without valves climbed more quickly in pressure over the 4 to 10 second range of inflation.

Many pneumatic cuff console or control systems are useable with a variety of cuff types. For example, one console could be useable with a Cuff Z, Cuff A, and Cuff C. But only Cuff Z is useable for the particular medical purpose the user is practicing, it would be useful for the user to be able to confirm that Cuff Z is attached. If Cuff Z has an integrated valve, then the console can quickly inflate the attached pneumatic cuff, generating a pressure curve, and confirm whether it is indeed Cuff Z with an integrated valve that is attached.

The method and systems discussed herein can allow for automatic verification of pneumatic cuff type, size, brand, or other variables. The use of a valve to generate unique pressure curves correlated to each type of pneumatic cuff allows a processor to evaluate and compare the generated pressure curve and verify whether the correct pneumatic cuff is attached.

Figure 9:
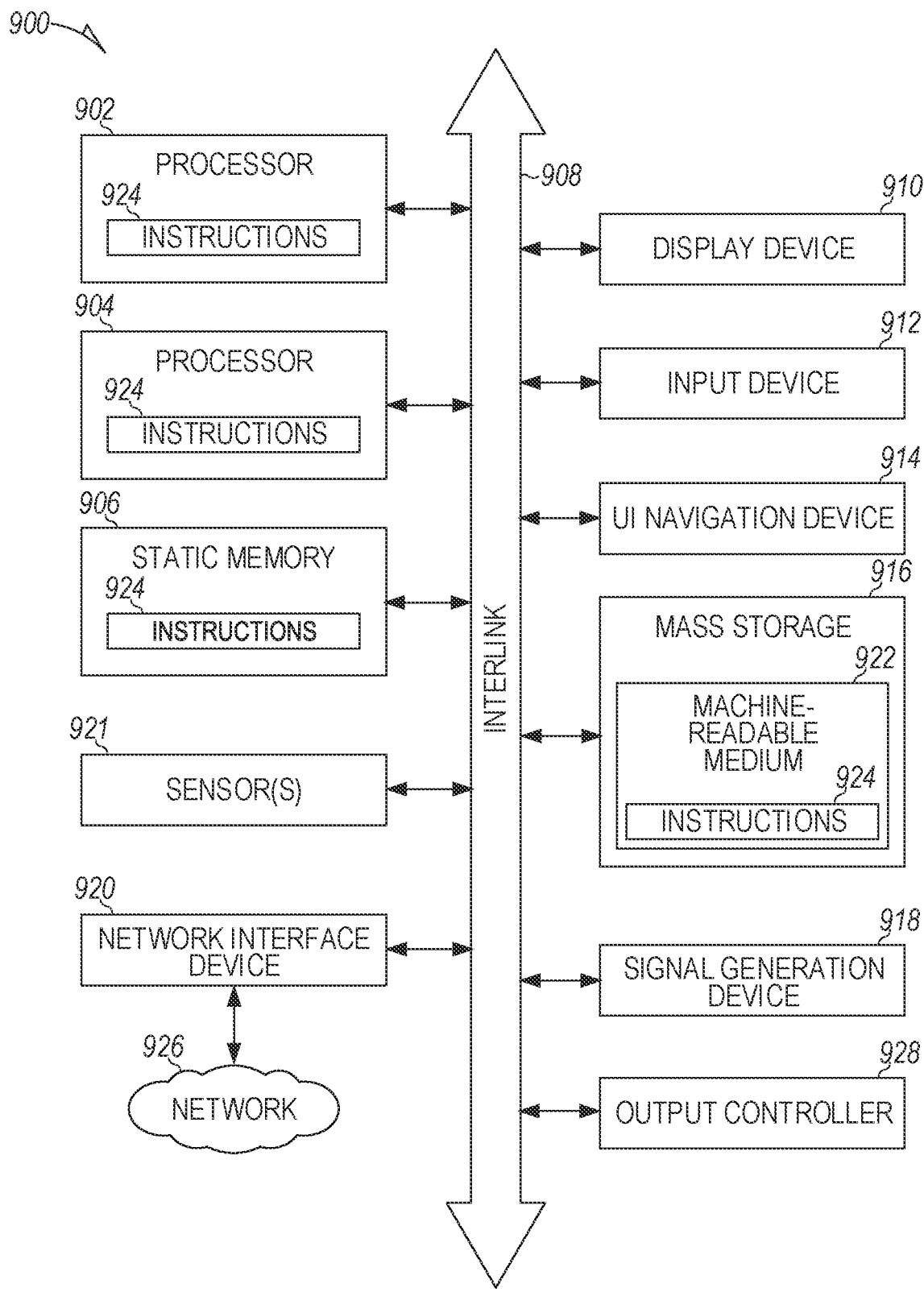
FIG. 9 illustrates a block diagram of an example machine upon which any one or more of the techniques discussed herein can perform in accordance with some examples.

FIG. 9 illustrates a block diagram of an example machine (e.g., console) 900 upon which any one or more of the techniques discussed herein can perform in accordance with some examples. Machine 900 can be, for example, the console shown in FIG. 1, or other computer or inflation device that can inflation a pneumatic cuff, sense and record pressure curves produced during inflation of that pneumatic cuff, determine the type of pneumatic cuff attached to the machine, induce an inflation profile or parameter, or combinations thereof.

In alternative examples, the machine 900 can operate as a standalone device or can be connected (e.g., networked) to other machines. In a networked deployment, the machine 900 can operate in the capacity of a server machine, a client machine, or both in server-client network environments. In an example, the machine 900 can act as a peer machine in peer-to-peer (P2P) (or other distributed) network environment. The machine 900 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system or console) 900 can include a hardware processor 902 (e.g., a central processing unit (CPU), a graphics processing unit (GPU), a hardware processor core, or any combination thereof), a main memory 904 and a static memory 906, some or all of which can communicate with each other via an interlink (e.g., bus) 908.

The machine 900 can further include a display unit 910, an alphanumeric input device 912 (e.g., a keyboard), and a user interface (UI) navigation device 914 (e.g., a mouse). In an example, the display unit 910, input device 912 and UI navigation device 914 can be a touch screen display. The machine 900 can additionally include a storage device (e.g., drive unit) 916, a signal generation device 918 (e.g., a speaker), a network interface device 920, and one or more sensors 921, such as a global positioning system (GPS) sensor, compass, accelerometer, or another sensor. The machine 900 can include an output controller 928, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 916 can include a machine readable medium 922 on which is stored one or more sets of data structures or instructions 924 (e.g., software) embodying or utilized by any one or more of the techniques or functions described herein. The instructions 924 can also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 can constitute machine readable media.

While the machine readable medium 922 is illustrated as a single medium, the term "machine readable medium" can include a single medium or multiple medium (e.g., a centralized or distributed database, and/or associated caches and servers) configured to store the one or more instructions 924. The term "machine readable medium" can include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine-readable medium examples can include solid-state memories, and optical and magnetic media.

The instructions 924 can further be transmitted or received over a communications network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMAX®), IEEE 802.15.4 family of standards, peer-to-peer (P2P) networks, among others. In an example, the network interface device 920 can include one or more physical jacks (e.g., Ethernet, coaxial, or phone jacks) or one or more antennas to connect to the communications network 926. In an example, the network interface device 920 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

VARIOUS NOTES & EXAMPLES

Each of these non-limiting examples can stand on its own or can be combined in various permutations or combinations with one or more of the other examples.

Example 1 can include a system comprising: a pneumatic cuff with a valve, a console connectable to the pneumatic cuff, the console comprising a processor and memory including instructions, which when executed by the processor cause the processor to: inflate the pneumatic cuff through the integrated valve past a threshold pressure such that the integrated valve opens; receive sensor data indicative of a pressure curve during inflation of the pneumatic cuff; compare the pressure curve to stored pressure curves; determine a recommendation, based on the comparison, including verification of the type of pneumatic cuff; and output the recommendation to a user.

Example 2 can include Example 1, wherein the pneumatic cuff is a tourniquet cuff, a deep vein thrombosis compression cuff, or a blood pressure cuff.

Example 3 can include any of Examples 1-2, wherein the valve comprises a valve system.

Example 4 can include any of Examples 1-3, wherein the pneumatic cuff is a child cuff or an adult cuff.

Example 5 can include any of Examples 1-4, wherein the pneumatic cuff is adapted for an arm or a leg.

Example 6 can include any of Examples 1-5, wherein the valve is a flap valve adjacent a pressure bump, wherein the flap valve is adapted to open past the pressure bump at the threshold pressure.

Example 7 can include any of Examples 1-6, wherein the valve is a cross-slit valve adapted to open at the threshold pressure.

Example 8 can include any of Examples 1-7, wherein the valve is a z-shaped valve having a first side and a second side, and wherein the first side is adapted to open during inflation at a predetermined threshold pressure, and the second side is adapted to open during deflation.

Example 9 can include any of Examples 1-8, wherein the valve further comprises a support member connecting the first side and the second side.

Example 10 can include any of Examples 1-9, wherein the pneumatic cuff is a tourniquet cuff and the threshold pressure comprises about 100 mm Hg to about 250 mm Hg.

Example 11 can include any of Examples 1-10, wherein the pneumatic cuff is a tourniquet cuff a target inflation pressure comprises about 100 mm Hg to about 600 mm Hg.

Example 12 can include at least one non-transitory machine-readable medium including instructions, which when executed by a processor of a console, cause the processor to: determine whether the pneumatic cuff is connected to the console; initiate a procedure to inflate the pneumatic cuff; generate a pressure curve associated with the inflation of the pneumatic cuff; and verify, upon analysis of the pressure curve, a type of pneumatic cuff attached.

Example 13 can include Example 12, wherein the procedure to inflate the pneumatic cuff comprises inflating to a pre-determined threshold pressure.

Example 14 can include any of Examples 12-13, wherein the pre-determined threshold pressure causes a valve in the pneumatic cuff to open.

Example 15 can include any of Examples 12-14, wherein the pressure curve is a stepped curve.

Example 16 can include any of Examples 12-15, wherein analysis of the pressure curve comprises comparing the generated pressure curve with a library of pressure curves.

Example 17 can include any of Examples 12-16, wherein analysis of the pressure curve comprises generating a positive response if the pressure curve has been determined to be representative of a desired cuff type.

Example 18 can include a method comprising: inflating a pneumatic cuff through a pneumatic pathway comprising a valve, wherein inflating comprises providing a fluid to the pneumatic cuff at pressure level above the threshold pressure such that the valve opens; receiving sensor data regarding pressure in the pneumatic pathway; generating a pressure profile based on the sensor data; inputting the pressure profile into a model; and determining a type of pressure cuff based on the model.

Example 19 can include Example 18, wherein the console pumps air at a consistent rate.

Example 20 can include any of Examples 18-19, further comprising recording the sensor data in a memory associated with the console.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A system comprising:
   a pneumatic cuff with an integrated valve;
   a console connectable to the pneumatic cuff, the console comprising a processor and memory including instructions, which when executed by the processor cause the processor to:
   inflate the pneumatic cuff through the integrated valve past a threshold pressure such that the integrated valve opens;
   receive sensor data indicative of a pressure curve during the inflation of the pneumatic cuff;
   compare the pressure curve to a dynamic database of stored pressure curves using a classifier produced by a neural network algorithm;
   determine a recommendation, based on the comparison, including verification of a type of the pneumatic cuff; and
   output the recommendation to a user.

2. The system of claim 1, wherein the pneumatic cuff is a tourniquet cuff, a deep vein thrombosis compression cuff, or a blood pressure cuff.

3. The system of claim 1, wherein the pneumatic cuff is a child cuff or an adult cuff.

4. The system of claim 1, wherein the pneumatic cuff is adapted for an arm or a leg.

5. The system of claim 1, wherein the integrated valve is a flap valve adjacent to a pressure bump, wherein the flap valve is adapted to open past the pressure bump at the threshold pressure.

6. The system of claim 1, wherein the integrated valve is a cross-slit valve adapted to open at the threshold pressure.

7. The system of claim 1, wherein the pneumatic cuff is a tourniquet cuff and the threshold pressure is in a range of 100 mm Hg to 250 mm Hg.

8. The system of claim 7, wherein the tourniquet cuff has a target inflation pressure that is in a range of 100 mm Hg to 600 mm Hg.

9. The system of claim 1, wherein the instructions, which when executed by the processor of a console, cause the processor to produce the database of stored pressure curves with the neural network algorithm.

10. The system of claim 9, wherein the instructions, which when executed by the processor of a console, cause the processor to:
    set up an initial database of multiple different pressure curves corresponding to different pneumatic cuff types;
    generate characteristic features of the multiple different pressure curves;
    select a subset of the characteristic features of the multiple different pressure curves;
    produce at least one eigenvector based on the subset of the characteristic features; and
    derive the classifier.

11. The system of claim 10, wherein the instructions, which when executed by the processor of the console, cause the processor to: generate and select the characteristic features comprises using supervised principal component analysis and independent component analysis.

12. The system of claim 10, wherein the at least one eigenvector contains information for distinguishing between types of pressure curves in the dynamic database of stored pressure curves.

13. The system of claim 10, wherein the instructions which when executed by the processor of the console, cause the processor to: apply the classifier to determine the recommendation.

14. A system comprising:
    a pneumatic cuff with an integrated valve, wherein the integrated valve is a z-shaped valve having a first side and a second side, and wherein the first side is adapted to open during inflation at a predetermined threshold pressure, and the second side is adapted to open during deflation;
    a console connectable to the pneumatic cuff, the console comprising a processor and memory including instructions, which when executed by the processor cause the processor to:
    inflate the pneumatic cuff through the integrated valve past the predetermined threshold pressure such that the integrated valve opens;
    receive sensor data indicative of a pressure curve during the inflation of the pneumatic cuff;
    compare the pressure curve to stored pressure curves;
    determine a recommendation, based on the comparison, including verification of a type of the pneumatic cuff; and
    output the recommendation to a user.

15. The system of claim 14, wherein the z-shaped valve further comprises a support member connecting the first side and the second side.

* * * * *